United States Patent [19]

Bowlin

[11] Patent Number: 5,013,719
[45] Date of Patent: May 7, 1991

[54] METHOD OF EFFECTING IMMUNOSUPPRESSION

[75] Inventor: Terry L. Bowlin, Maineville, Ohio

[73] Assignee: Merrell Dow Pharmaceuticals Inc., Cincinnati, Ohio

[21] Appl. No.: 193,847

[22] Filed: May 13, 1988

[51] Int. Cl.$^5$ ............................................. A61K 37/02
[52] U.S. Cl. ...................................... 514/11; 514/549; 514/551; 514/561; 514/885
[58] Field of Search ................. 514/2, 9, 11, 549, 551, 514/561, 885

[56] References Cited

U.S. PATENT DOCUMENTS

| | | | |
|---|---|---|---|
| 4,117,118 | 9/1978 | Harri et al. | 424/177 |
| 4,139,563 | 2/1979 | Metcalf et al. | 424/244 |
| 4,413,141 | 11/1983 | Bey et al. | 424/319 |
| 4,499,072 | 2/1985 | Sunkara et al. | 424/85.7 |

OTHER PUBLICATIONS

Talmadge et al., 13th International Congress of Chemotherapy, Vienna, pp. 203/18–203/35 (1983).
Bowlin et al., Biol. Abst., vol. 82, No. 10528 (1986).
Bowlin et al., Biol. Abstr., vol. 83, No. 35700 (2/15/87).
Webb, "Immunosuppression and Immunopotentiation", Basic & Clinical Immunology, Lange Medical Publications, pp. 260–262 and 248 (1976).
Oppenheim et al., Cellular Functions in Immunity and Inflammation, Elsevier/North-Holland, New York, p. 293 (1981).
Saydjari et al., [in JNCI (1986) 77, 1087].
Britton and Palacios [in Immunological Rev. (1982) 65, 5].
Bey et al., [in J. Med. Chem. (1983) 26, 1551].
Bowlin et al., [in Cellular Immunol. (1987) 105, 110].
Calabresi, P. et al., Goodman and Gilman's *The Pharmacological Basis of Therapeutics*, Chapter 55, 7th Edition: 1298–99 (1985).
Borel, J. F. et al., *Transplantation Proceedings*, 15, Supplement 1 and 2: 2207–3188 (1983).
Weinblatt et al., *Arthritis and Rheumatism*, 30: 11 (1987).
Dougados, M. et al., *Arthritis and Rheumatism* 30: 83 (1987).
Stiller et al., *Science* 223: 1362 (1984).
Nussenblatt et al., *Lancet II:* 235–38 (1983).

*Primary Examiner*—John Doll
*Assistant Examiner*—Christina Chan
*Attorney, Agent, or Firm*—Louis J. Wille

[57] ABSTRACT

This invention relates to a method of effecting immunosuppression in a patient in need thereof, comprising co-administering to said patient an effective amount of an immunosuppressive agent, wherein said immunosuppressive agent is not an ornithine decarboxylase inhibitor, and an effective amount of an ornithine decarboxylase inhibitor.

1 Claim, No Drawings

METHOD OF EFFECTING IMMUNOSUPPRESSION

FIELD OF THE INVENTION

This invention relates to a method of treating a patient to effect immunosuppression.

BACKGROUND OF THE INVENTION

The immune system is one of the primary defenses against disease bearing microbes and other foreign antigens in higher animals. An immune response is mediated by the action of specific immune cells which react to specific antigens. Potential antigens can be a variety of substances, often proteins, which are foreign to an individual's body. They are most frequently located on the outer surfaces of cells. Potential antigens can be found on pollen grains, tissue grafts, animal parasites, viruses, and bacteria.

In humans, many potential antigens never pass the body's first two defense lines and therefore never trigger the immune system. These two defense lines consist firstly of the skin, mucous membranes, tears, and stomach acid and secondly of specialized white blood cells, granulocytes and monocytes, and macrophages which destroy pathogens and other potential antigens by phagocytosis, that is, by engulfing and destroying the foreign material. These white blood cells and macrophages are called phagocytes. When pathogens or other foreign substances do pass the body's first two defense lines, the immune response begins.

There are two principal immune defense systems, humoral and cellular, both of which react to antigens. Humoral immunity is due to circulating antibodies which are found in the gamma globulin fraction of the plasma proteins. When plasma is centrifuged at high speeds its component proteins separate by weight into sections called fractions. Antibodies are usually found in the fraction whose components have a molecular weight of approximately 156,000. This particular fraction has been named the gamma globulin fraction. Humoral immunity forms a major defense against bacterial infections. Cellular immunity is partly due to lymphocyte products called lymphokines. This type of immunity is responsible for delayed allergic reactions, rejection of transplants of foreign tissue, and rejection of tumor cells. It is the major defense against infections due to viruses, fungi, and a few bacteria such as the tubercle bacillus.

Specialized white blood cells called lymphocytes are responsible for both humoral and cellular immunity. Lymphocyte precursor cells are made in the bone marrow of adult humans followed by migration to various organs or in the yolk sac of a developing fetus followed by migration into the fetus and then to various organs. In humans, some of these precursor cells migrate to the thymus, which is a two-lobed, glandular appearing structure located in the upper chest just behind the sternum, where they are transformed into T-lymphocytes, which are involved in cellular immunity. In humans, the rest of the precursor cells migrate to the spleen where they are transformed into B-lymphocytes, which are involved in humoral immunity. The T- and B-lymphocytes are structurally indistinguishable although they function differently and can be distinguished through various chemical means. The mature lymphocytes circulate in the blood and can also be found in the lymph nodes as well as the spleen and thymus.

Humoral immunity is mediated by the B-lymphocytes which have receptors for particular antigens on their cell surfaces. They seem to be very specific and each type of B-lymphocyte reacts to only one antigen. When bacteria or viruses, for example, invade an organism, B-lymphocytes react to and combine with the antigens on the bacterial or viral surface and the lymphocyte is stimulated to divide. Its daughter cells are transformed into specialized cells called plasma cells. These cells produce and then secrete large quantities of antibodies into the general circulation. The antibodies are specific for the antigens which stimulated their production and react only with those antigens. Antibodies known as agglutinins cause several antigen containing substances to agglutinate or clump together. This keeps the substance from spreading to the tissues and allows the phagocytes to capture or the lymph nodes to filter the invading material. Other antibodies act by opening holes in bacterial cell walls, thereby killing the bacteria. These are known as lysins. Antibodies call antitoxins combine with toxins produced by bacteria and thereby neutralize them.

Once a pathogen invades the body and the immune response begins, antibodies can be made in several hours. This initial reaction is called the primary response or primary immunization. However, during that time, the pathogens have also been dividing and sometimes producing toxin, either of which results in various disease symptoms. It may take days or weeks before enough antibodies are made to eliminate all the pathogens but once they disappear, the disease symptoms disappear as well. The lymphocytes, plasma cells, and antibodies remain and circulate in the blood so that if the same pathogens enter the body a second time, the lymphocytes react immediately and start antibody production. The response of the sensitized lymphocytes is called the secondary response. The secondary response results in the production of higher levels of antibody than were produced during the primary response. So many antibodies are produced so rapidly that the microbes are unable to divide and cause disease. This type of humoral immunity is known as immediate hypersensitivity due to the fact that a previously exposed organism can respond within minutes to an antigen, as in the case of hay fever. Another example of immediate hypersensitivity would be anaphylactic shock, an extreme allergic reaction that sometimes occurs when an individual is exposed to an antigen to which he has been sensitized. At times, this humoral response to the antigen can result in death.

Humoral immunity can be both naturally and artificially induced. In the case of active natural immunity, an individual's lymphocytes continue to circulate and activate the production of antibodies after an infection. This active natural immunity lasts for many years or even a lifetime. An infant receives antibodies from the colostrum, milk secreted by the mother, the first few days after birth, which gives it immunity the first year of its life. This is known as passive natural immunity since the infant is not involved in the actual production of the antibodies. Active artificial immunity is induced by injecting dead or weakened microbes into an individual. Their surface antigens can still trigger lymphocyte production of antibodies but these microbes do not cause the disease symptoms that their more virulent forms do. When the individual is later exposed to the virulent microbe, he is already sensitized and immediately responds with a massive production of antibodies. Active artificial immunity may last many years or permanently with booster shots. There is also a form of passive artificial immunity which provides protection for about one month. This temporary immunity is brought about by injecting antibodies obtained from another person or animal into an individual. It is usually only used in crisis situations and epidemics. Because the lymphocytes are bypassed, they neither make antibodies nor "remember" the antigen, which accounts for the temporary effect of this method.

In cellular immunity, as contrasted to humoralimmunity, circulating antibodies are not detectable. The T-lymphocytes which mediate this type of immunity are activated when they encounter antigens on cells from another individual, as in the case of transplants, tumors, or viruses. Like B-lymphocytes, T-lymphocytes are specific and each type reacts with only one antigen. The lymphocytes enlarge, divide, and produce lymphokines which participate in the attack on the foreign antigen. They also stimulate the phagocytic activity of macrophages. Although immunological memory exists as with humoral immunity, the response is much slower. It may take as long as ten or twelve hours to develop a response in a previously sensitized individual and cellular immunity is therefore known as delayed hypersensitivity. The allergic reaction to poison ivy, oak, and sumac, the red splotch seen in a positive tuberculin skin test, and rejection of transplant tissue are all cellular immune responses.

Immunomodulating agents activate or inhibit the process of lymphocyte proliferation. Normal lymphocyte proliferation is due to various interactions between antigens, macrophages, T- and B-lymphocytes as well as certain chemicals. For example, the presence of a particular antigen activates a particular T- or B-lymphocyte. Additionally, certain B-lymphocytes can be activated by active T-lymphocytes while others are independent of the T-lymphocytes and are activated only by antigens. Activated T-lymphocytes can cause macrophages to produce a molecule known as interleukin 1(IL-1) which in turn activates both T- and B-lymphocytes. Activated T-lymphocytes can also produce a molecule known as interleukin 2(IL-2) which further induces T-lymphocyte activation. Chemicals, called mitogens can trigger DNA synthesis and mitosis, which are signs of activity in T- or B-lymphocytes. Some mitogens affect only one type of lymphocyte while others affect many types. Immunomodulating agents of various kinds and in varying amounts affect the complex interactions between the components of the immune system. Some immunosuppressive agents, such as (2R, 5S or 5R-)-6-heptyne-2,5-diamine, hereinafter referred to as MAP, are inhibitors of ornithine decarboxylase. Other immunosuppressive agents, such as cyclosporin A (CsA) or corticosteroids, for example, prednisone, are not inhibitors of ornithine decarboxylase.

Ornithine decarboxylase is involved in the biosynthesis of polyamines and catalyzes the conversion of the amino acid ornithine to the polyamine putrescene. Putrescene serves as a precursor to polyamines spermidine and spermine and additionally has been shown to have a marked regulatory effect upon the polyamine biosynthetic pathway. Although the exact physiologic role of polyamines has not been clearly delineated, there is evidence to suggest that polyamines are involved with cell division and growth and that increased synthesis of putrescene is the first indication that a tissue will undergo renewed growth processes. Hence, inhibitors of ornithine decarboxylase, such as MAP, are useful as immunosuppressive agents.

Although the immune system is a major defense against substances which can cause disease, it cannot distinguish between helpful and harmful foreign substances and destroys both. It would be useful in many instances to have a means of regulating the immune system without harming the individual.

There are times when the individual's immunological response causes more damage or discomfort than the invading microbes or foreign material, as in the case of allergic reactions. Suppression of the immune response in these case would be desirable.

Occasionally, the immunological mechanisms become sensitized to some part of the individual's own body causing interference with or even destruction of that part. The ability to distinguish between "self" and "not self" is impaired and the body begins to destroy itself. This can result in an autoimmune disease. Some examples of these autoimmune diseases in man are rheumatoid arthritis, certain hemolytic anemias, rheumatic fever, thyroiditis, ulceractive colitis, myestheniagravis, glomerulonephritis—a kidney disease, allergic encephalo-myelitis, continuing nerve and liver destruction which sometimes follows viral hepatitis, and possibly multiple sclerosis and systemic lupus erythematosus. Some forms of autoimmunity come about as the result of trauma to an area usually not exposed to lymphocytes such as neural tissue or the lens of the eye. When the tissues in these areas become exposed to lymphocytes, their surface proteins can act as antigens and trigger the production of antibodies and cellular immune responses which then begin to destroy those tissues. Other autoimmune diseases develop after exposure of the individual to antigens which are antigenically similar to, that is cross-react with, the individual's own tissue. Rheumatic fever is an example of this type of disease in which the antigen of the streptococcal bacterium which causes rheumatic fever is cross-reactive with parts of the human heart. The antibodies cannot differentiate between the bacterial antigens and the heart muscle antigens and cells with either of those antigens can be destroyed. Suppression of the immune system in these autoimmune diseases would be useful in minimizing or eliminating the effects of the disease.

Circulating antibodies and cellular immune responses play a role in the rejection of transplanted tissues and organs. Unless the donor is the identical twin of the recipient or is the individual himself, the recipient's lymphocytes recognize the transplant as "not self" and immediately respond to destroy it. The exceptions to this situation are transplants to non-vascularized areas (privileged sites), such as the cornea of the eye, where lymphocytes do not circulate and therefore are not sensitized and do not prompt an immune response. It is currently difficult to suppress the immune reaction to prevent rejection of the transplant without severely damaging the patient in other ways. The patient must also be given massive doses of antibiotics because his own defenses against infection have been suppressed. Suppression of the immune system would thus be useful in preventing such rejection of transplant tissues.

SUMMARY OF THE INVENTION

The present invention provides an improved method of effecting immunosuppression in a patient in need thereof, comprising co-administering to said patient an effective amount of an immunosuppressive agent, wherein said immunosuppressive agent is not an ornithine decarboxylase inhibitor, and an effective amount of an ornithine decarboxylase inhibitor.

DETAILED DESCRIPTION OF THE INVENTION

According to the present invention, an ornithine decarboxylase inhibitor is a compound which irreversibly inhibits the enzyme ornithine decarboxylase in vitro as determined by the method of Bey et al., (J. Med. Chem. 26, 1551 (1983)). One skilled in the art can, by use of the above method, readily determine whether a particular compound is, or is not, an ornithine decarboxylase inhibitor. Compounds such as α-difluoromethylornithine, hereinafter referred to as α-DFMO, and MAP, and the like, are well known and appreciated as ornithine decarboxylase inhibitors.

MAP is disclosed by Metcalf, B. W., and Jung, M., in U.S. Pat. No. 4,139,563 which is hereby incorporated herein by reference. Compounds such as MAP are disclosed as having immunosuppressant properties. α-DFMO is disclosed by Bey, P., and Jung, M., in U.S. Pat. No. 4,413,141 which is hereby incorporated herein by reference. α-DFMO and MAP are the preferred ornithine decarboxylase inhibitors according to the present invention.

According to the present invention, an immunosuppressive agent is a compound such as CsA or a corticosteroid, for example, prednisone, which is known and appreciated by those of ordinary skill in the art as having immunosuppressive properties. CsA and prednisone are the preferred immunosuppressive agents according to the present invention. CsA is most preferred as the immunosuppresive agent. Neither CsA nor corticosteroids such as prednisone are ornithine decarboxylase inhibitors as defined according to the present invention.

CsA is disclosed by Harri, E., and Ruegger, A., in U.S. Pat. No. 4,117,118 which is hereby incorporated herein by reference. CsA is a fungal metabolite which inhibits interleukin-2 production and thereby inhibits generation of cytolytic T-lymphocytes. CsA has found widespread acceptance as an immunosuppressant in organ transplantation. However, adverse effects such as nephrotoxicity and hepatotoxicity have been reported during CsA treatment (See Britton, S., and Palacios, R., Immunol. Rev. 65, 5 (1982)).

The present invention provides a method for synergistically effecting immunosuppression in a patient in need thereof at a reduced dose of CsA. This improved method therefore provides a means for reducing the adverse effects associated with CsA treatment while effecting immunosuppression.

As used herein, the term "patient" refers to a warm-blooded animal such as a mammal which is afflicted with a disease, such as an allergic reaction or autoimmune disease, or is in danger of rejection of a transplanted tissue or organ. It is understood that humans are included within the scope of the term "patient". Based on standard clinical and laboratory tests and procedures, an attending diagnostician, as a person skilled in the art, can readily identify those patients who are in need of treatment with immunosuppressive agents.

The improved method of treatment according to the present invention comprises co-administering an effective amount of at least one immunosuppressive agent, which is not an ornithine decarboxylase inhibitor, and an effective amount of at least one ornithine decarboxylase inhibitor. As used herein, the term "co-administering" refers to concomitant treatment with an immunosuppressive agent, which is a non-ornithine decarboxylase inhibitor, and an ornithine decarboxylase inhibitor. It is contemplated that treatment can be in either separate or combined dosage forms. The term "concomitant treatment" contemplates simultaneous administration of the immunosuppressive agent and the ornithine decarboxylase inhibitor, as well as staged administration. Thus, the patient may be pretreated with one of the co-administered agents, for example, with an ornithine decarboxylase inhibitor, prior to initiation of the concomitant treatment with the other agent. The method(s) and times(s) of administration of the agent(s) and inhibitor(s) will be controlled by the skilled diagnostician so that the desired therapeutic effect and/or blood levels of each is co-existent.

When an immunosuppressive agent and an ornithine decarboxylase inhibitor are administered according to the present invention, a synergistic immunosuppressive effect is obtained. This synergistic effect can result in a degree of immunosuppression which is greater than the additive immunosuppressive effects of the agent and inhibitor when solely administered. Additionally, it has been discovered that, according to the present invention, the dose of the immunosuppressive agent required to obtain a particular degree of immunosuppression will be lower when the immunosuppressive agent is co-administered with an ornithine decarboxylase inhibitor, rather than when the immunosuppressive agent is administered alone. This surprising reduction in the necessary dose of an immunosuppressive agent, such as CsA, provides a very beneficial and desirable concomitant decrease in the known adverse effects associated with such agent, such as nephrotoxicity and hepatotoxicity.

The effective amounts of an ornithine decarboxylase inhibitor and an immunosuppressive agent can readily be determined by an attending diagnostician, as one skilled in the art, by evaluating a number of relevant factors including, but not limited to, the species of mammal, its size, age and general health, the specific disease or purpose involved, the specific ornithine decarboxylase inhibitor and immunosuppressive agents selected, the mode of administration, the bioavailability characteristics of the preparation or preparations administered, the dose regimen selected, and the use of any concomitant medication. The correct amount of the immunosuppressive agent and the ornithine decarboxylase inhibitor can be readily determined in any specific situation by one skilled in the art, by using conventional range finding techniques and analogous results observed under other circumstances. An effective amount of an immunosuppressive agent will vary from about 0.1 milligrams per killogram per day (mg/kg/day) to about 500 mg/kg/day. An effective amount of an ornithine decarboxylase inhibitor will vary from about 5 mg/kg/day to about 5 grams (g)/kg/day. More specifically, a preferred effective amount of CsA will vary from about 1 mg/kg/day to about 20 mg/kg/day; a preferred effective amount of prednisone will vary from about 0.2 mg/kg/day to 25 about 200 mg/kg/day; a preferred effective amount of α-DFMO will vary from about 5 mg/kg/day to about 500 mg/kg/day; a preferred effective amount of MAP will vary from about 5 mg/kg/day to about 500 mg/kg/day.

Generally, the immunosuppressive agent and the ornithine decarboxylase inhibitor can be administered in proportions of about 1:1 to about 1:500 by weight, respectively, and more preferably in proportions of about 1:1 to about 1:50 by weight, respectively.

In effecting conjunctive therapy according to the present invention, the immunosuppressive agent and the ornithine decarboxylase inhibitor can be administered orally or parenterally in any manner which makes them bioavailable in effective amounts including, for example, orally, intraperitoneally, subcutaneously, or intravenously. One skilled in the art can readily determine the bioavailability of various forms of the preparations using standard techniques and procedures. Oral or intravenous administration is preferred.

The immunosuppressive agent and the ornithine decarboxylase inhibitor can be co-administered according to the present invention in the form of pharmaceutical compositions. These pharmaceutical compositions comprise an effective amount of an immunosuppressive agent and/or the ornithine decarboxylase inhibitor in admixture with one or more pharmaceutically acceptable excipients. A single pharmaceutical composition may contain both the immunosuppressive agent and the ornithine decarboxylase inhibitor or a separate pharmaceutical composition for each of the immunosuppressive agent and the ornithine decarboxylase inhibitor may be prepared. The pharmaceutical compositions can be prepared in a conventional manner well known and appreciated in the art of pharmaceutical science.

Pharmaceutically acceptable excipients are substances which are chemically inert to the active compounds and have no detrimental side effects or toxicity to mammals under the conditions of use. Suitable excipients include solvents, such as water, alcohol and propylene glycol, carriers, surface active agents, suspending agents, lubricants, binders, disintegrants, flavors, colorants and the like. Such carriers and excipients are known to those skilled in the art and are disclosed, for example, in texts such as *Remington's Pharmaceutical Manufacturing*, 13th Edition, Mack Publishing Co., Easton, Pa. (1965).

In order to illustrate the method of the present invention, the following example is provided. This example is illustrative only and is not intended to limit the scope of the invention in any way.

EXAMPLE 1

Effect of α-DFMO and CsA on Cytolytic T-Lymphocyte Induction In Vivo

Alloreactive cytolytic T-lymphocytes (CTL) are generated in vivo by injecting C57BL/6 mice intraperitoneally with allogenic P815 (H-$2^d$) cells ($10^7$) on day 0.

The injected animals are placed in one of the following three treatment groups and are treated for 10 days: (1) α-DFMO (2% in drinking water on days 1 through 10; approximately 3 g/kg/day), (2) CsA (oral dose of CsA on days 1, 3, 5, 7 and 9, 0.25, 2.5, 25 or 250 mg/kg/day) or (3) α-DFMO (2% in drinking water on days 1 through 10; approximately 3 g/kg/day) and CsA (oral dose of CsA on days 1, 3, 5, 7 and 9; 0.25, 2.5, 25 or 250 mg/kg/day).

Splenic cytolytic activity, which represents a direct measurement of immune response, is assessed by a 4-hour $^{51}$Cr release assay as described by Bowlin et al., Cell. Immunol. 105, 110 (1987). Effector cells are characterized as T-cells based on surface phenotype (Thy 1.2+, Lyt 2.2+, L3T4−) and allo-specificity (H-$2^d$) as described by Bowlin et al., Cell Immunnol. 105, 110 (1987).

As shown in Table 1, the results of this study indicate that conjunctive therapy of α-DFMO (approximately 3 g/kg/day) and CsA (approximately 2.5 mg/kg/day and above) provides a substantially increased immunosuppressive effect over that produced by α-DFMO or CsA alone. This synergistic effect is particularly apparent at CsA doses of 2.5 and 25 mg/kg/day.

TABLE 1

The effect of α-difluoromethylornithine and cyclosporin A on cytolytic T lymphocyte induction in vivo

| Treatment[a] | Cytolytic T Lymphocyte Induction[b] % Inhibition (mean ± S.E., n = 3) |
|---|---|
| DFMO (2%) | 10 ± 0.5 |
| CsA (0.25 mg/kg) | 0 ± 0 |
| DFMO (2%) + CsA (0.25 mg/kg) | 10 ± 0.5 |
| CsA (2.5 mg/kg) | 8 ± 0.4 |
| DFMO (2%) + CsA (2.5 mg/kg) | 35 ± 1.5[c] |
| CsA (25.0 mg/kg) | 11 ± 0.6 |
| DFMO (2%) + CsA (25.0 mg/kg) | 56 ± 3.0[c] |
| CsA (250 mg/kg) | 76 ± 3.5[c] |
| DFMO (2%) + CsA (250 mg/kg) | 90 ± 4.5[c] |

[a]C57BL/6 mice were injected with allogeneic P815 cells on day 0. DFMO was administered continuously, starting on day 1, in drinking water. CsA was administered p.o. on days 1, 3, 5, 7, and 9.
[b]Splenic cytolytic T lymphocyte activity was assessed on day 10 utilizing $^{51}$Cr labeled P815 target cells. Data is expressed as % inhibition compared with vehicle treated control.
[c]p < 0.001.

I claim:
1. A method of effecting immunosuppression in a patient in need thereof, comprising co-administering to said patient an effective amount of cyclosporin A and an effective amount of α-DFMO.

* * * * *

UNITED STATES PATENT AND TRADEMARK OFFICE
CERTIFICATE OF CORRECTION

PATENT NO. : 5,013,719
DATED : May 7, 1991
INVENTOR(S) : Terry L. Bowlin

It is certified that error appears in the above-identified patent and that said Letters Patent is hereby corrected as shown below:

```
Column 6, Line 62 patent reads:  "/ day to 25 about 200" and
should read --/ day to about 200"
```

Signed and Sealed this

Fifteenth Day of December, 1992

Attest:

DOUGLAS B. COMER

*Attesting Officer*     Acting Commissioner of Patents and Trademarks